United States Patent [19]

Engel et al.

[11] 4,279,898

[45] Jul. 21, 1981

[54] IN VIVO INHIBITORS OF CHOLESTEROL BIOSYNTHESIS

[75] Inventors: Robert R. Engel, Carle Place; Virender K. Sarin, New York; Barry Gotlinksy, Bronx; Burton E. Tropp, Manhasset Hills; Thomas S. Parker, New York, all of N.Y.

[73] Assignee: Research Foundation of the City University of New York, New York, N.Y.

[21] Appl. No.: 142,631

[22] Filed: Apr. 22, 1980

[51] Int. Cl.$^3$ ...................... A01N 57/00; A01N 45/00
[52] U.S. Cl. .................................... 424/217; 424/238; 260/397.1; 260/397.5
[58] Field of Search .......................... 260/397.1, 397.5; 424/217, 238

[56] References Cited

U.S. PATENT DOCUMENTS

| 4,104,285 | 8/1978 | Torres et al. | 260/397.1 |
| 4,107,188 | 8/1978 | Torres et al. | 260/397.1 |

Primary Examiner—Elbert L. Roberts
Attorney, Agent, or Firm—John S. Roberts, Jr.

[57] ABSTRACT

Dialkyl esters of 5-carbo[etiocholane-3′α-7′α, 12′α-trihydroxy-17′β(1″ methyl-4′ butyl]oxy-4-hydroxy-4-methylpentyl-1-phosphonate and 5-carbohexadecyloxy-4-hydroxy-4-methylpentyl-1-phosphonate are shown to inhibit cholesterol biosynthesis in rat liver cells. Preparation of the active compounds is given.

6 Claims, No Drawings

IN VIVO INHIBITORS OF CHOLESTEROL BIOSYNTHESIS

The invention described herein was made in the course of work under a grant or award from the Department of Health and Human Services.

STATEMENT OF PRIOR ART

Publications by the inventors disclose the preparation of 5-carboxy-4-hydroxy-4-methylpentyl-1-phosphonic acid and inhibition of 5-phosphomevalonate kinase by this isosteric analogue of 5-phosphomevalonate. See "Inhibition of 5-Phosphomevalonate Kinase by an Isosteric Analogue of 5-Phosphomevalonate," *American Chemical Society*, 1978, pp. 8014–8016, and "Isosteres of Natural Phosphates. 7. The Preparation of 5-Carboxy-4-hydroxy-4-methylpentyl-1-phosphonic Acid," *Tetrahedron Letters*, No. 4 (1977), pp. 351–354.

BACKGROUND

Phosphonic acids have long been under investigation as analogue materials in a variety of biosynthetic functions and particularly with a view to inhibiting the function. The inclusion of a methylene group in place of a normal esteric phosphate oxygen has been investigated. Terpene biosynthesis and the inhibition of phosphomevalonate kinase have been studied.

The present invention is concerned with compounds which specifically inhibit cholesterol biosynthesis in vivo. Specifically, dialkyl phosphonate esters which include an etiocholane derivative esterified with the terminal carboxylic acid and cetyldecyl derivatives are useful.

The following examples illustrate the preparation.

EXAMPLE 1

Preparation of an etiocholane derivative which is utilized in forming the compound shown in Example 3.

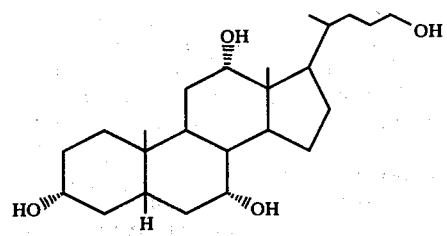

Preparation of 17β-(1-methyl-4-hydroxybutyl) etiocholane-3α,7α,12α-triol.

To 20 g (49 mmol) of cholic acid in 75 mL of anhydrous ether and 75 mL of tetrahydrofuran, freshly distilled over lithium aluminum hydride, was added 1.86 g (49 mmol) of lithium aluminum hydride at room temperature. The mixture was heated with stirring at 70° for 18 hr. After cooling, the excess lithium aluminum hydride was destroyed by the addition of 25 mL of water in a dropwise manner. The reaction mixture was filtered and the solid washed with ether and tetrahydrofuran. The combined organic materials were dried over sodium sulfate and concentrated under reduced pressure. The resultant precipitate was filtered, washed with water, and dried under vacuum to yield 12 g (62%) of the above-named compound of mp 224°–225°.

EXAMPLE 2

This compound is used in the preparation of the inhibitor produced in Example 3.

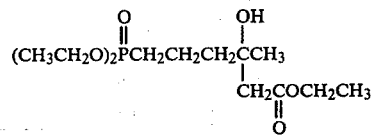

Preparation of Diethyl 5-carboethoxy-4-hydroxy-4-methylpentyl-1-phosphonate.

In a 100 mL three-necked flask equipped with two addition funnels, a gas inlet tube, a magnetic stirrer, and a septum was placed 20 mL of anhydrous ether which was cooled to −23° under a nitrogen atmosphere. Freshly distilled diisopropylamine (2.22 g, 22 mmol) was added via a syringe followed by a solution of n-butyllithium in hexane (13.2 mL, 22 mmol) which was added over a period of 10 min. through an addition funnel. After stirring for 1 hr., the bath temperature was reduced to −78° and dry ethyl acetate (2.16 mL, 220 mmol) was added dropwise. The solution was stirred for 30 min. at −78° and then there was added 4.88 g (22 mmol) of diethyl 4-oxopentyl-1-phosphonate. After 30 min. the reaction mixture was treated with 4.0 mL of 20% hydrochloric acid and allowed to warm to room temperature; the mixture was diluted with 4 mL of distilled water and extracted 4 times with 20 mL portions of ether. The organic extracts were combined, dried over anhydrous sodium sulfate, and the solvent evaporated under reduced pressure to yield 3.53 g (52%) of the above-named compound as a viscous oil. NMR(CCl4) 0.9-18 δ (m, 16 H), 1.8–2.7 δ (singlet on multiplet, 4H), 3.2–4.3 δ (m, 7 H). IR(CCl4, cm$^{-1}$) 3550, 3050, 1735, 1460, 1410, 1390, 1250, 1175, 1060, 1040, 950.

EXAMPLE 3

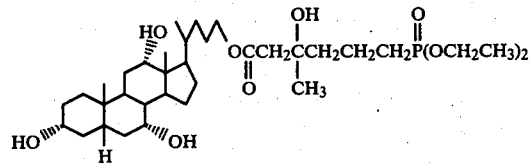

Preparation of Diethyl 5-carbo[etiocholane-3'α,7'α,12'α-trihydroxy-17'β-(1"-methyl-4"-butyl)]oxy-4-hydroxy-4-methylpentyl-1-phosphonate.

To 0.50 g (2.0 mmol) of diethyl 5-carboxy-4-hydroxy-4-methylpentyl-1-phosphonate in dry pyridine was added 1.25 g (4.1 mmol) of triisopropylbenzenesulfonyl chloride. This mixture was stirred at 0° for 40 min. after which time 0.79 g of 17-(1-methyl-3-hydroxybutyl)etiocholane-3α,7α,12α-triol (2.0 mmol) was added. The mixture was stirred for 2 hr. at 0° C. after which it was poured into 15 mL of ice water. The resulting precipitate was filtered and purified by column chromatography on silica eluting first with 9:1 chloroform-ethanol to remove by-products followed by 95% ethanol to yield 0.41 g (31% of the above-named compound. Traces of silica in the product were removed by dissolution in chloroform, filtration through a milli-pore filter, and evaporation of the solvent under reduced pressure. Found: C, 63.88; H, 9.37. Calculated for $C_{35}H_{63}O_9P$: C, 63.81; H, 9.64%.

EXAMPLE 4

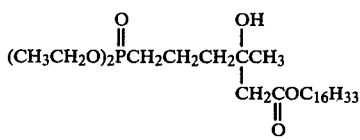

Preparation of Diethyl 5-carbohexadecyloxy-4-hydroxy-4-methylpentyl-1-phosphonate.

Diethyl 5-carboxy-4-hydroxy-4-methylpentyl-1-phosphonate (2.82 g, 10.0 mmol) was dissolved in 15 mL of water containing 0.84 g (10.0 mmol) of sodium bicarbonate. It was allowed to stir at room temperature for 30 min. after which the water was evaporated under reduced pressure with mild heating to 40°. The residue, after drying under vacuum (0.01 Torr) for 2 days, was dissolved in 17 mL of anhydrous dimethylformamide and heated to 80°. To this heated solution was added 3.05 g (10.0 mmol) of cetyl bromide and the heating was continued for 20 hr. in a stoppered flask. The dimethylformamide was removed under reduced pressure and there was then added to the residue 15 mL of ether and 15 mL of water. The organic layer was separated, dried over sodium sulfate, and the solvent evaporated under reduced pressure. The residue was purified by placement on a silica gel column and eluted first with chloroform to remove unreacted cetyl bromide, followed by a solution of 90:10 chloroform-ethanol. The fraction containing the desired compound was filtered through a milli-pore filter to yield 3.0 g (60%) of the above-named compound which exhibited a single spot of $R_f=0.72$ on silica with 90:10 chloroform-ethanol. NMR (CCl$_4$) 0.8–2.2 δ (m, 46 H), 2.4 δ (s, 2 H), 3.5–4.4 δ (m, 7 H). IR(CCl$_4$, cm$^{-1}$) 3700–3100, 3000, 1740, 1450, 1390, 1250, 1200, 1060, 1040, 950. Found: C, 63.73; H, 11.15. Calculated for $C_{27}H_{55}O_6P$: C, 63.99; H, 10.94%.

BIOLOGICAL TESTING

The materials from Examples 3 and 4 were tested using S$_{10}$ proteins from the 10,000 g supernatant of homogenized rat liver supplemented with cofactors and incubated under nitrogen. The activity of the agent was measured by comparison of carbon dioxide release and phosphate uptake upon addition of natural substrate to the enzyme system. The procedure employed is conventional and is the same as discussed in "Inhibition of 5-Phosphomevalonate Kinase by an Isosteric Analogue of 5-Phosphomevalone," *American Chemical Society* (1978), pp. 8014–8016. The cholesterol biosynthesis is inhibited by the present claimed compounds and an operating range for said compounds is 5–50 mg/kg of tissue weight.

The 10,000 g supernatant of homogenized rat liver (S$_{10}$) contains all the enzymes needed to convert mevalonate to sterols.

The rate of inhibition was unexpectedly rapid.

Data has been gained through the use of the material with a specific carbon-14 label with rat liver hepatocytes. Here the material is shown to be taken up from solution by the cells which are performing the cholesterol biosynthesis in the liver.

What is claimed is:

1. Dialkyl 5-carbo[etiocholane-3'α,7'α,12'α-trihydroxy-17'β (1" methyl-4" butyl]oxy-4-hydroxy-4-methylpentyl-1-phosphonate wherein the alkyl group contains 1 to 8 carbon atoms.

2. A compound of claim 1 wherein the alkyl group is ethyl.

3. The use of an effective amount of diethyl 5-carbo[etiocholane-3'α,7'α,12'α-trihydroxy-17'β (1" methyl-4" butyl]oxy-4-hydroxy-4-methylpentyl-1-phosphonate for the inhibition of cholesterol synthesis in rat liver cells.

4. The use according to claim 3 wherein the effective amount of the compound is in the range of 5–50 mg/kg of tissue weight.

5. A process for the preparation of the compound of claim 2 comprising the steps of:
   (1) reacting diethyl 5-carboxy-4-hydroxy-4-methylpentyl-1-phosphonate in dry pyridine with triisopropylbenzenesulfonyl,
   (2) adding to the reaction an equimolar quantity compared to the phosphonate of 17β (1-methyl-3-hydroxybutyl)etiocholane-3α,7α,12α-triol and reacting for 2 hours at 0° C.,
   (3) filtering the reaction mixture to recover the compound of claim 2 as a precipitate,
   (4) purifying the compound by column chromatography on silica with 9:1 chloroform-ethanol to remove by-products.

6. The use of diethyl 5-carbohexadecyloxy-4-hydroxy-4-methylpentyl-1-phosphonate for the inhibition of cholesterol synthesis in rat liver cells.

* * * * *